(12) United States Patent
Steiner et al.

(10) Patent No.: US 7,722,608 B2
(45) Date of Patent: May 25, 2010

(54) ALLOGRAFT IMPLANT WORKSTATION

(75) Inventors: Anton J. Steiner, Wharton, NJ (US); James Shock, Glen Rock, NJ (US); Paul J. Mulhauser, New York, NY (US); Karl D. Kirk, III, New York, NY (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 528 days.

(21) Appl. No.: 11/712,972

(22) Filed: Mar. 2, 2007

(65) Prior Publication Data

US 2008/0215052 A1 Sep. 4, 2008

(51) Int. Cl.
*A61B 17/56* (2006.01)

(52) U.S. Cl. .............................. 606/53; 606/54; 606/86; 269/54.1

(58) Field of Classification Search ............. 606/53–54, 606/79, 86; 269/54.1–54.3, 87.1–87.3, 37, 269/40–45

See application file for complete search history.

(56) References Cited

U.S. PATENT DOCUMENTS 4,807,863 A * 2/1989 Yang ........................... 269/153
6,640,666 B2 * 11/2003 Pliley .............................. 81/6

* cited by examiner

*Primary Examiner*—Eduardo C Robert
*Assistant Examiner*—Christina Negrelli
(74) *Attorney, Agent, or Firm*—John S. Hale; Gipple & Hale

(57) ABSTRACT

A portable surgical workstation for implant formation comprising a base with a central planar section. The central planar section has a plurality of tracks and a throughgoing slot with a recessed stepped surrounding surface formed on a bottom surface of the central planar section. A vise assembly mounted to the base comprises a fixed jaw member secured to the base, a traveling jaw member moveably mounted to the base and a fixed drive housing mounted to the base. The traveling jaw member has a plurality of rail members adapted to be slidably mounted in the central planar section tracks. The fixed drive housing has a threaded longitudinal bore which receives a threaded drive shaft, one end of the drive shaft being secured in the traveling jaw member to transport the traveling jaw members.

19 Claims, 8 Drawing Sheets

ALLOGRAFT IMPLANT WORKSTATION

RELATED APPLICATIONS

There is no related application.

STATEMENT REGARDING FEDERALLY SPONSORED RESEARCH OR DEVELOPMENT

Not applicable.

REFERENCE TO SEQUENCE LISTINGS A TABLE OR A COMPUTER PROGRAM LISTING COMPACT DISC APPENDIX

None.

BACKGROUND OF THE INVENTION

1. Field of Invention

The present invention is generally directed toward an implant workstation and is more specifically directed toward a surgical workstation for producing an allograft cartilage implant plug having a cartilage face and bone body.

2. Description of the Prior Art

Articular cartilage injury and degeneration present medical problems to the general population which are constantly addressed by orthopedic surgeons. Every year in the United States, over 500,000 arthroplastic or joint repair procedures are performed. These include approximately 125,000 total hip and 150,000 total knee arthroplastics and over 41,000 open arthroscopic procedures to repair cartilaginous defects of the knee.

In the knee joint, the articular cartilage tissue forms a lining which faces the joint cavity on one side and is linked to the subchondral bone plate by a narrow layer of calcified cartilage tissue on the other. Articular cartilage (hyaline cartilage) consists primarily of extracellular matrix with a sparse population of chondrocytes distributed throughout the tissue. Articular cartilage is composed of chondrocytes, type II collagen fibril meshwork, proteoglycans and water. Active chondrocytes are unique in that they have a relatively low turnover rate and are sparsely distributed within the surrounding matrix. The collagens give the tissue its form and tensile strength and the interaction of proteoglycans with water give the tissue its stiffness to compression, resilience and durability. The hyaline cartilage provides a low friction bearing surface over the bony parts of the joint. If the cartilage lining becomes worn or damaged resulting in lesions, joint movement may be painful or severely restricted. Whereas damaged bone typically can regenerate successfully, hyaline cartilage regeneration is quite limited because of it's limited regenerative and reparative abilities.

Articular cartilage lesions generally do not heal, or heal only partially under certain biological conditions due to the lack of vascularity. The limited reparative capabilities of hyaline cartilage usually results in the generation of repair tissue that lacks the structure and biomechanical properties of normal cartilage. Generally, the healing of the defect results in a fibrocartilaginous repair tissue that lacks the structure and biomedical properties of hyaline cartilage and degrades over the course of time. Articular cartilage lesions are frequently associated with disability and with symptoms such as joint pain, locking phenomena and reduced or disturbed function. These lesions are difficult to treat because of the distinctive structure and function of hyaline cartilage. Such lesions are believed to progress to severe forms of osteoarthritis.

Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of hyaline-like tissue that withstands normal joint loading and activity over prolonged periods. Currently, the techniques most widely utilized clinically for cartilage defects and degeneration are not articular cartilage substitution procedures, but rather lavage, arthroscopic debridement, and repair stimulation. The direct transplantation of cells or tissue into a defect and the replacement of the defect with biologic or synthetic substitutions presently accounts for only a small percentage of surgical interventions. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

Transplantation of cells grown in culture provides another method of introducing a new cell population into chondral and osteochondral defects. Carticel® is a commercial process to culture a patient's own cartilage cells for use in the repair of cartilage defects in the femoral condyle marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2-5 weeks. Once cultivated, the cells are injected during a more open and extensive knee procedure into areas of defective cartilage where it is hoped that they will facilitate the repair of damaged tissue. An autologous periosteal flap with cambium layer is sutured around the defect to seal the transplanted cells in place and act as a mechanical barrier. Fibrin glue is used to seal the edges of the flap. This technique preserves the subchondral bone plate and has reported a high success rate. Proponents of this procedure report that it produces satisfactory results, including the ability to return to demanding physical activities, in more than 90% of patients and that biopsy specimens of the tissue in the graft sites show hyaline-like cartilage repair. More work is needed to assess the function and durability of the new tissue and determine whether it improves joint function and delays or prevents joint degeneration. As with the perichondrial graft, patient/donor age may compromise the success of this procedure as chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The osteochondral plugs are harvested from a lower weight-bearing area of lesser importance in the same joint. Reports of results of osteochondral plug autografts in a small numbers of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts carry the risk of immune response or disease transmission. Musculoskeletal Transplant Foundation (MTF) has preserved fresh allografts in a media that maintains a cell viability of around 50% at 35 days for use as implants. In the current technology frozen allografts lack cell viability and have shown a decreased amount of proteoglycan content, however, they are commonly used for large defects.

A number of United States patents have been specifically directed towards the manufacture of plugs or cores which are implanted into a cartilage defect. U.S. Pat. No. 6,591,591 issued Jul. 15, 2003 describes a precut bone plug for use in allograft core transplantation surgery which has a tissue bank harvest the graft using a coring trephine with teeth having an inner diameter between 0.5 mm to 0.1 to create a bone core with a hyaline cartilage layer in approximately 7.9 mm, 9.9 mm, 11.9 mm diameters. Alternatively a donor harvester having a cutter tube with a straight cutting edge windows and depth markings with a torque handle on the proximal end may be used to obtain an allograft core as is shown in U.S. Pat. No. 5,919,196 issued Jul. 6, 1999. U.S. Pat. No. 6,592,588 issued Jul. 15, 2003 discloses instruments for cutting a bone core by cutting or punching having collared pins disposed within the harvester for removal of the harvester cores.

U.S. Pat. No. 4,565,192 issued Jan. 21, 1986 shows a multi-plate device with fixed pins and movable pins for cutting a portion of a patella during knee surgery. U.S. Pat. No. 5,092,572 discloses an allograft vise with a "V" shaped vise face and moveable vise plates. The vise is affixed to a table and can be provided with spherical vise plates having a sharp tripod support for a femur.

U.S. Pat. Nos. 6,488,033 and 6,852,114 (a divisional application of the '033 patent) issued respectively Dec. 3, 2002 and Feb. 8, 2005 are directed toward an osteochondral transplant workstation for cutting a core out of an allograft bone held in an adjustable vise with a lubricated rotary cutting bit. The core is removed from the bit, held in a specially designed set of pliers, and cut to size by a saw blade to fit into a blind bore which has been oriented and drilled into the patient's arthritic defect area. This workstation while an improvement over existing procedure is cumbersome to use and requires experience and training use.

The present invention was designed to overcome prior art implant workstations and provide a simple to use portable core preparation workstation which allows a surgeon to custom cut the allograft core so that it snugly fits in the particular defect area of the patient being operated on.

SUMMARY OF THE INVENTION

A portable workstation for the preparation of osteochondral allograft cartilage implants, the workstation having a portable plastic base with a fixed jaw member mounted on the base and a traveling jaw member to hold an allograft hemi condyle being cut to provide replacement cores and the replacement core itself. A miter for a surgical saw is formed on one side of each jaw member allowing the replacement allograft core to be cut to an exact length for insertion into a patient.

It is an object of the invention to provide a portable surgical workstation for forming osteochondral allograft plugs with a cartilage layer which are of the correct size for insertion into a blind bore in a patients knee to repair a cartilage defect.

It is also an object of the invention to provide a portable surgical workstation allowing the creation of a cartilage repair implant which has a cartilage layer contoured to the defect site of a patient which is easily placed in a defect area by the surgeon to form a continuous cartilage surface in the patient's defect area.

It is still another object of the invention to provide a portable surgical workstation for creating a cartilage implant core during surgery which has load bearing capabilities.

It is further an object of the invention to provide a portable surgical workstation which can be easily used by the surgeon to create correctly dimensional and contoured cartilage implants.

It is yet another object of the invention to provide a portable surgical workstation which can be easily cleaned and sterilized.

It is still another object of the invention to provide a workstation with a miter so that accurate core lengths for the implant can be obtained.

It is a further object of the invention to provide a portable surgical workstation which holds a full or hemi condyle in a fixed stable position allowing a uniform core to be cut from the hemi condyle.

These and other objects, advantages, and novel features of the present invention will become apparent when considered with the teachings contained in the detailed disclosure along with the accompanying drawings.

DESCRIPTION OF THE INVENTION

The term "tissue" is used in the general sense herein to mean any transplantable or implantable tissue such as bone.

The terms "transplant" and "implant" are used interchangably to refer to tissue (xenogeneic or allogeneic) which may be introduced into the body of a patient to replace or supplement the structure or function of the endogenous tissue.

The terms "autologous" and "autograft" refer to tissue or cells which originate with or are derived from the recipient, whereas the terms "allogeneic" and "allograft" refer to tissue which originate with or are derived from a donor of the same species as the recipient. The terms "xenogeneic" and "xenograft" refer to tissue which originates with or are derived from a species other than that of the recipient.

The present invention is directed towards a cartilage repair implant forming workstation. The preferred embodiment and best mode of the invention is shown in FIGS. 1-13.

Figure 5:
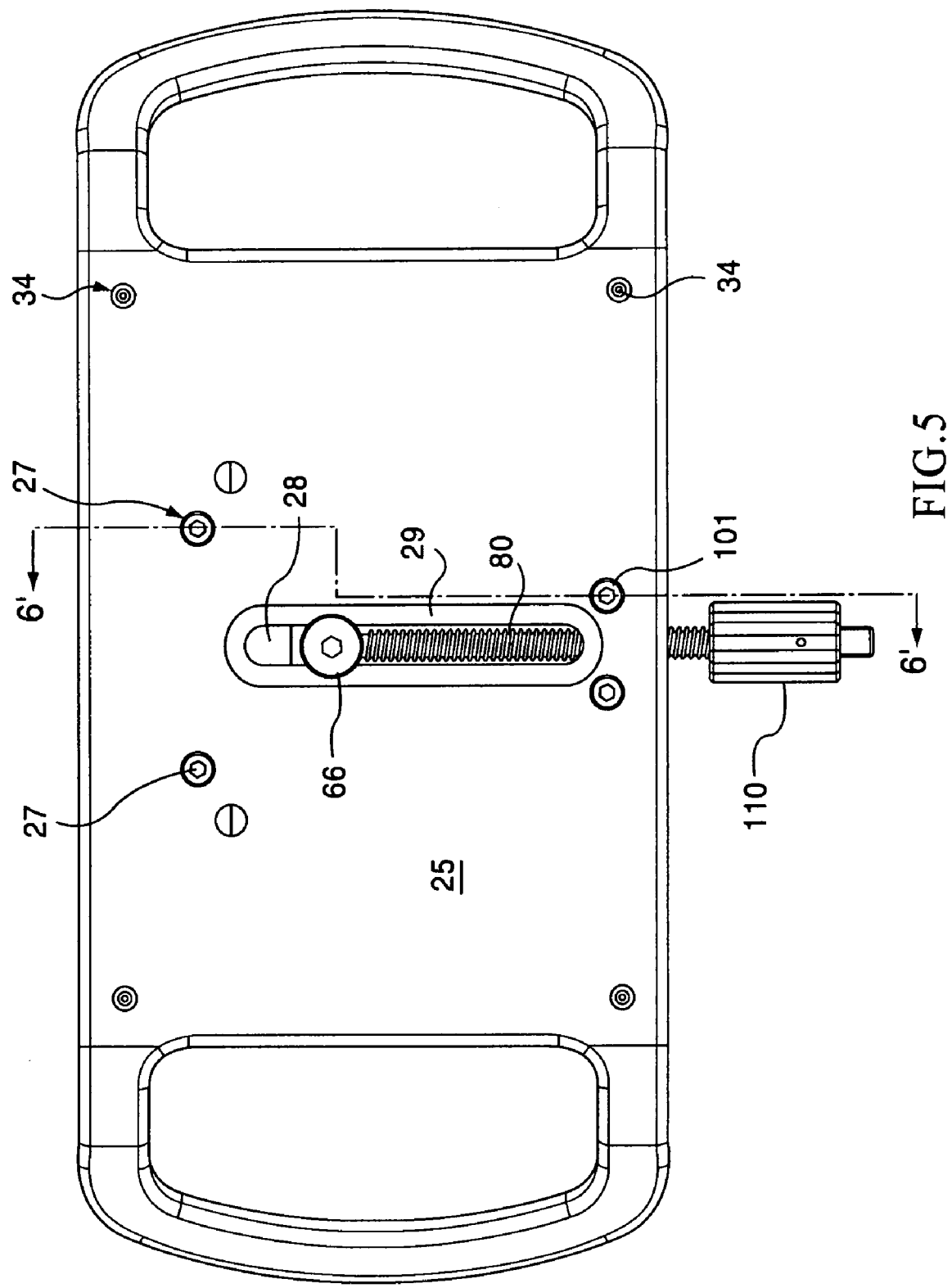
FIG. 5 is a bottom plan view of the workstation of FIG. 2.
Figure 8:
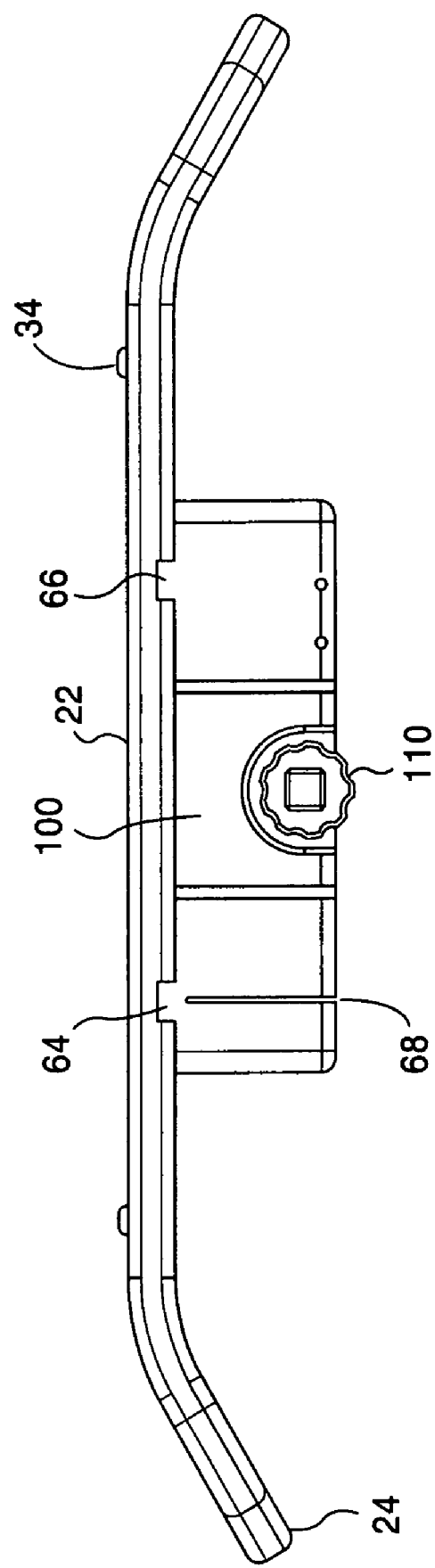
FIG. 8 is a side elevation view of the workstation shown in FIG. 5.
Figure 9:
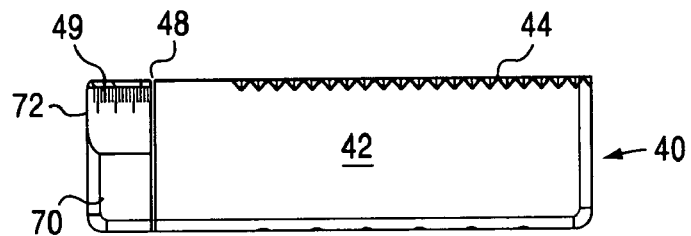
FIG. 9 is a top plan view of the stationary vice jaw shown in FIG. 1.
Figure 10:
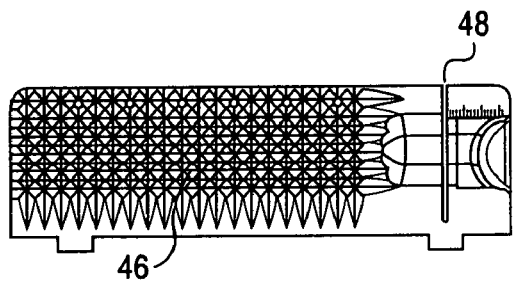
FIG. 10 is a front elevation view of the engaging face of the stationary vice jaw shown in FIG. 9.
Figure 11:
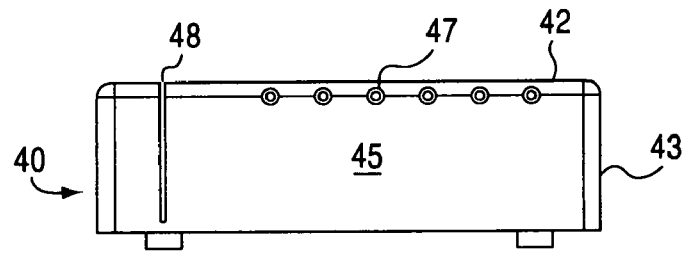
FIG. 11 is a front elevation view of stationary vice jaw shown in FIG. 9.
Figure 12:
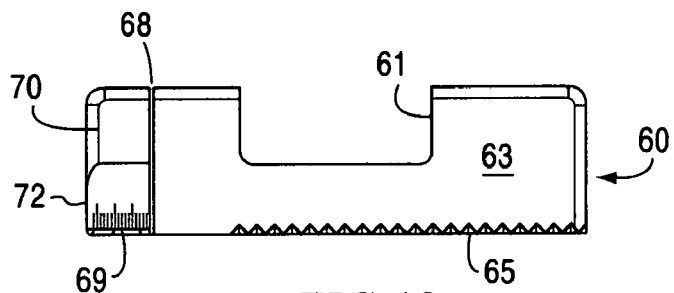
FIG. 12 is a top plan view of the traveling vice jaw shown in FIG. 1.
Figure 13:
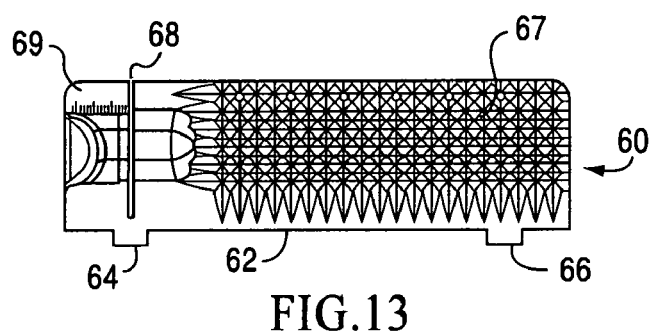
FIG. 13 is a front elevation view of the engaging face of the traveling vice jaw shown in FIG. 12.
Figure 14:
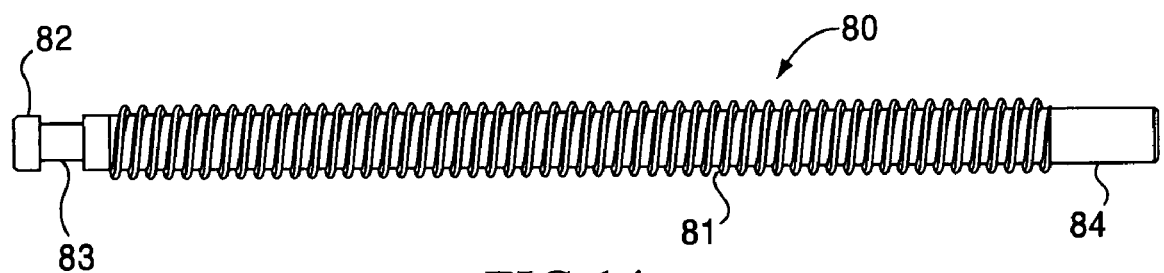
FIG. 14 is an enlarged side elevation view of the screw drive shaft for the traveling vice jaw.
Figure 15:
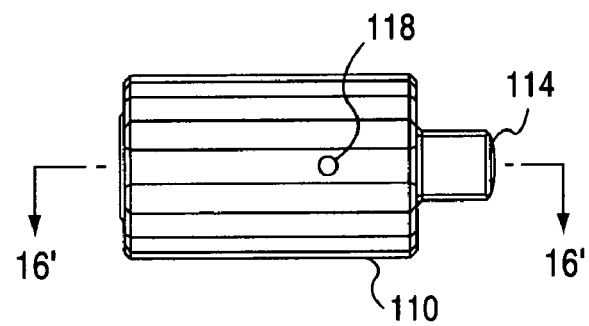
FIG. 15 is an enlarged side elevation view of the handle for the screw drive shaft shown in FIG. 14.

The portable workstation 20 is constructed with a plastic or metal base 22 having integral upwardly angled handles 24. The angled handles 24 define grasping cutouts 26 and the base 22 defines a centrally located slot 28 which has a surrounding cut away step portion from the bottom surface 25 as shown in FIG. 5 to receive a shoulder screw 66 which retains the traveling vice jaw 60 in the slot 28. Located on each side of slot 28 cut into the upper surface 23 of the base are tracks 30 and 32 which receive the rails 64 and 66 of the traveling jaw 60 as seen in FIG. 8. The bottom surface 25 of the base 22 is provided with small legs at each corner of the base 22 in the form of button head cap screws 34 which together with the grasping handles 24 provide stability to the workstation during the cutting operations.

Figure 6:
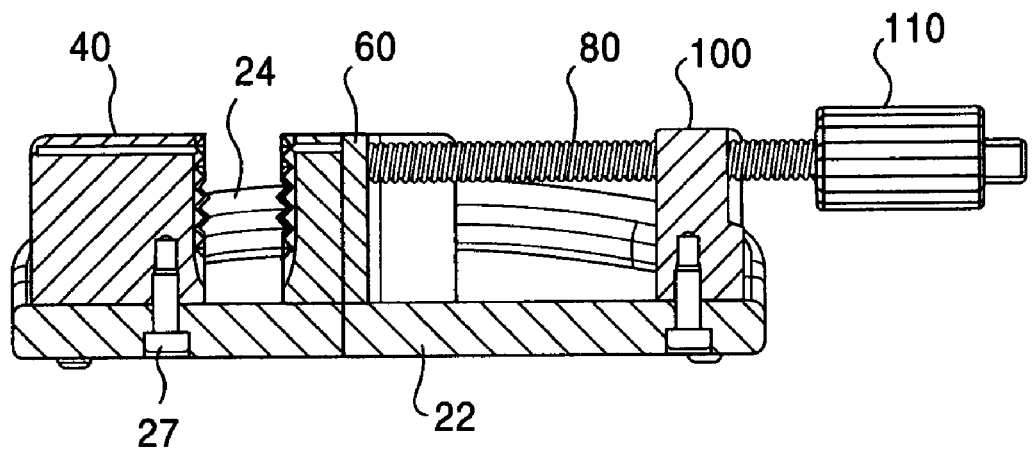
FIG. 6 is a cross sectional view taken along line 6'-6' on FIG. 5.
Figure 7:
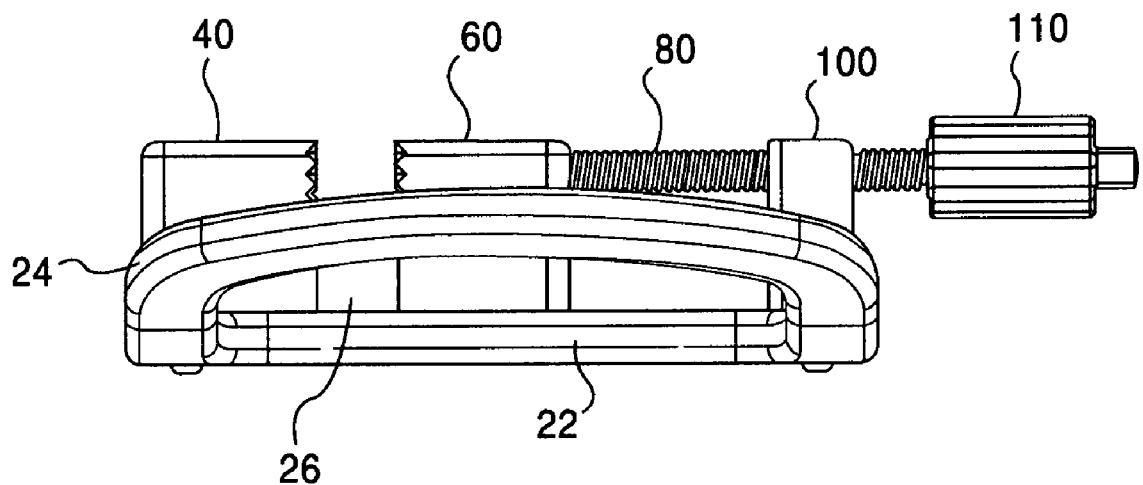
FIG. 7 is a right end elevation view of the workstation shown in FIG. 2.

Mounted on the upper surface 23 of base 22 by recessed socket head cap screws 27 as seen in FIG. 6 is a solid fixed vice jaw 40 of the vise assembly having a planar top surface 42, planar side surfaces 43, a rear grasping surface 44 and a front vertical planar surface 45. A plurality of anchor pin through holes 47 are cut through the vice jaw 40 to allow a workpiece to be anchored to the fixed jaw. The grasping surface 44 of fixed jaw 40 (or allograft work piece engaging surface) is formed with a square diamond knurl pattern 46 having adjacent teeth with a typical depth of 0.098 mm, a typical pitch of 0.197 mm and opposing wall angles of 90°. The grasping surface can receive the notch of an allograft hemi condyle which has been precut prior to surgery for easy insertion into the vise or a cut allograft core taken from the condyle. An end section of the fixed jaw has a saw slot 48 and laser engraved scale marking 49. The end section is formed with a flat planar section 70 and a downwardly angled flat surface 72 upon which the scale markings are placed.

A "U" shaped moveable or traveling jaw 60 is mounted on base 22. The traveling jaw 60 has a bottom surface 62 defining two parallel rails 64 and 66 which slide in the tracks 30 and 32 formed in top surface of the base 22 and defines a central recess 61.

The top surface 63 of the traveling jaw 60 is planar and the associated work piece grasping surface 65 (or allograft work piece engaging surface) is formed with a square diamond knurl pattern 67. The knurl pattern has adjacent teeth with a typical depth of 0.098 mm, a typical pitch of 0.197 mm and opposing wall angles of 90°. The grasping surface can receive the notch of the allograft hemi condyle which has been precut prior to surgery for easy insertion into the vise. An end section of the traveling jaw defines a saw slot 68 and laser engraved scale markings 69.

Each jaw member 40, 60 defines an aligned miter slot 48, 68 which establishes a perpendicular cut for the allograft core being cut. The miter slot is of sufficient width to receive a standard type surgical saw blade. The top surface of each of each jaw portion adjacent the respective miter slot has a flat planar section 70 and a downward angled flat surface 72 provided with respective scale markings 49, 69 set to the allograft plug length in millimeters.

Figure 1:
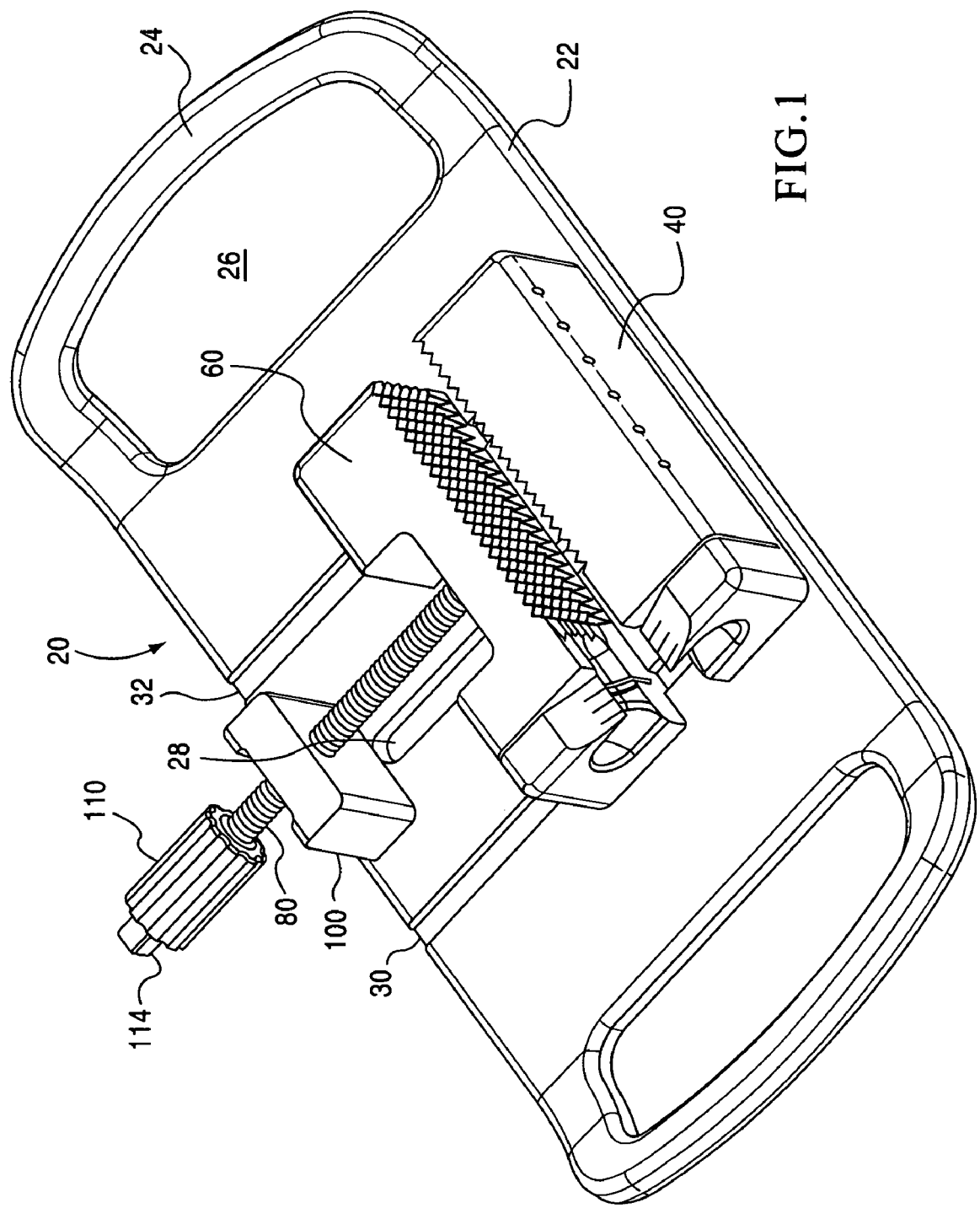
FIG. 1 is a perspective view of the inventive surgical workstation.
Figure 2:
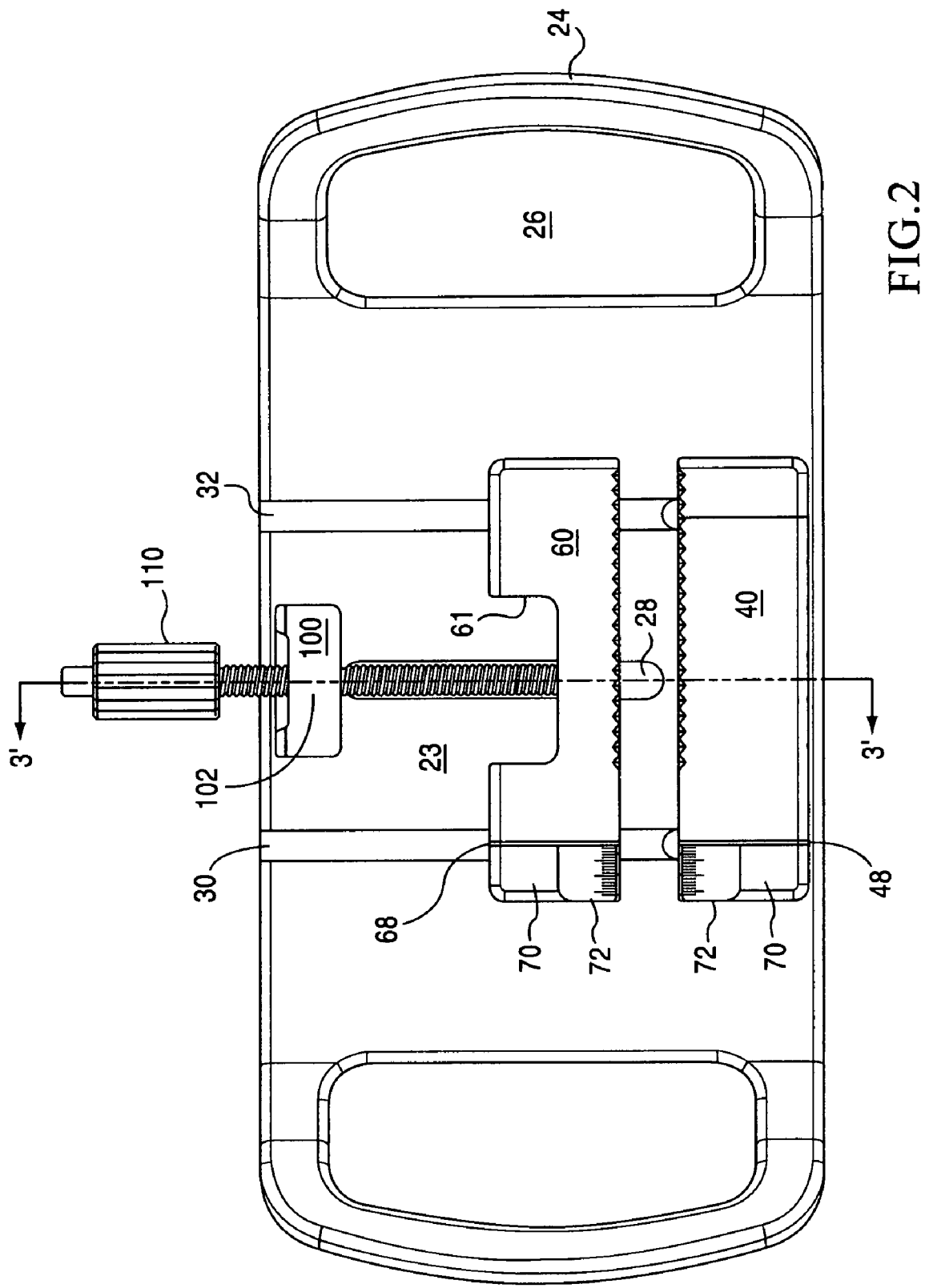
FIG. 2 is a top plan view of the workstation of FIG. 1.
Figure 3:
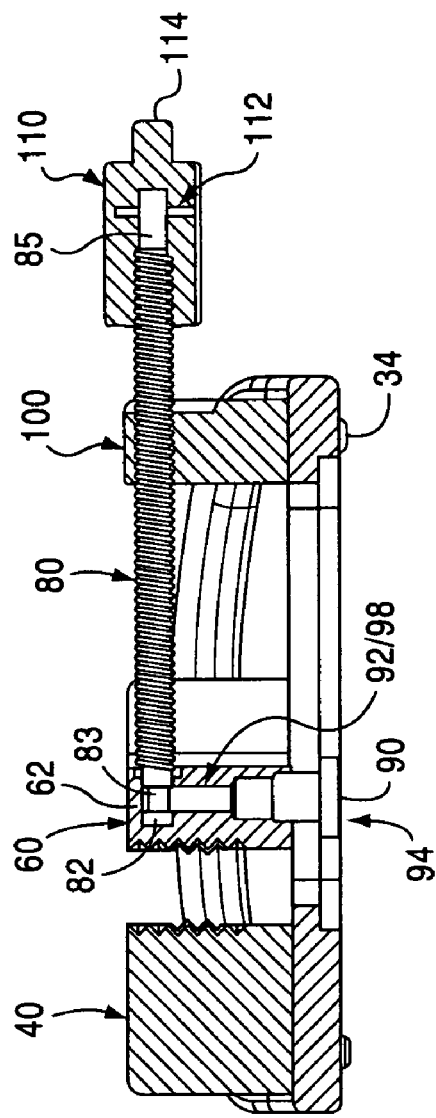
FIG. 3 is a cross sectional view of the workstation of FIG. 2 taken along line 3'-3'.
Figure 4:
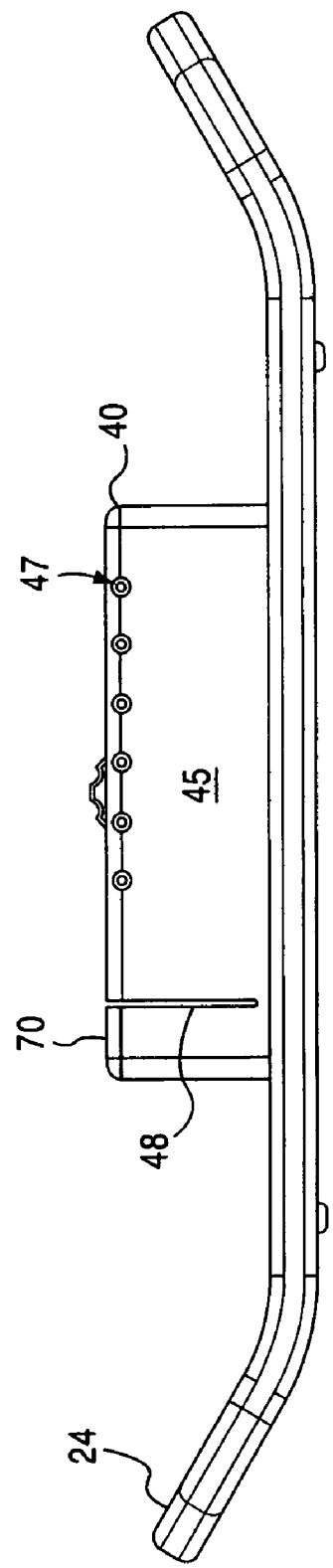
FIG. 4 is a side elevation view of the workstation of FIG. 2.

As shown in FIG. 3, a blind bore 62 is cut into the central section of the traveling jaw 60 axially parallel to the plane of the base to receive an unthreaded end 82 of screw shaft 80 having a threaded shaft portion 81. A shoulder screw 90 is positioned in a stepped bore which is transverse to the blind bore 62 and communicates with same. The distal end 92 of the shoulder screw 90 is mounted in a channel 83 cut in the shaft end 82, the proximal end or head 94 of the shoulder screw being seated on top surface of the step 29 surrounding slot 28. The head 94 of the shoulder screw has a greater diameter than the width of slot 28. If desired a pin 98 can take the place of distal end 92 and can be use to engage the distal end of the shoulder screw rather than the same being integrally formed with the shoulder screw.

Figure 16:
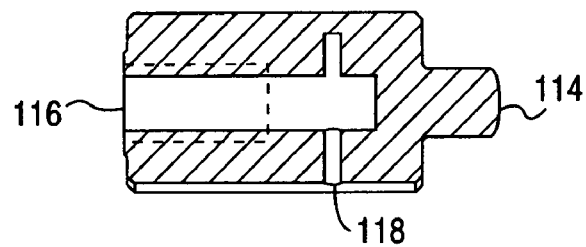
FIG. 16 is a cross sectional view of the handle of FIG. 15 taken along line 16'-16' of FIG. 15.

A fixed screw block 100 is mounted to the upper surface 23 of base 22 by recessed screws 101 as seen in FIG. 5. The fixed screw block 100 has a threaded through going bore 102 cut through it to receive threaded shaft portion 81. The thread on the shaft portion 81 is an acme or convention type thread. The proximal end 84 of shaft 80 has a handle 110 mounted thereto via blind bore 116, the handle being held in place by a securement cross pin 112 which is placed through a transverse blind bore 118 in the handle as shown in FIG. 16. The handle 110 is permanently pinned to shaft 80. The proximal end of the handle 110 defines a wrench lug 114 which is adapted to receive a slotted wrench tool for tightening the vise.

In operation, the lesion or defect is removed by cutting a counterbore in the patient of a predetermined diameter and depth in the defect area with a cannulated boring bit. An allograft hemi condyle is placed between the fixed and traveling jaws of the vise of the workstation to hold the condyle in the desired position. A donor cutting guide is placed over the allograft condyle in the same position and orientation as the original cartilage removed from the defect area and then a coring bit and arbor is used to obtain an allograft plug of the same diameter as the diameter of the core cut into the defect area of the patient. The plug is then trimmed to length by the surgical saw in the miter cutting area.

The implant plug which has been cut to the desired length in the workstation is placed in the bore which has been cut in the lesion area of the bone of the patient with the upper surface of the cartilage cap being slightly proud or substantially flush with the surface of the original cartilage remaining in the area. The length of the osteochondral plug can be the same as the depth of the bore or less than the depth of the bore The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. A portable surgical workstation for implant formation comprising a base, a vise assembly mounted to said base, said base comprising a central planar section defining a plurality of tracks and handles secured to and extending away from said central planar section at an angle to a plane of said central planar section, said vise assembly comprising a fixed jaw member secured to said base and a traveling jaw member moveably mounted to said base, said traveling jaw member defining a plurality of rail members adapted to be slidably mounted in said central planar section tracks, a fixed drive housing mounted to said base, drive means moveably mounted to said fixed drive housing and seated in said traveling jaw member for transporting said traveling jaw member toward and away from said fixed jaw member, each jaw member defining a slot across its width which is axially aligned with the slot of the opposing jaw member of a width and depth to receive a surgical saw and a workpiece grasping face formed on each of said jaw members.

2. A portable surgical workstation as claimed in claim 1 wherein said handles define cutouts and are integral with said central planar section.

3. A portable surgical workstation as claimed in claim 1 wherein said fixed drive housing defines a threaded longitudinal bore which receives said drive means, said drive means comprising a threaded drive shaft, one end of said drive shaft being mounted in said traveling jaw member to preclude axial movement of said drive shaft within said traveling jaw member while retaining rotational movement.

4. A portable surgical workstation as claimed in claim 1 wherein said fixed jaw member and said traveling jaw member each define a grasping surface which is knurled.

5. A portable surgical workstation as claimed in claim 4 wherein said grasping knurled surface comprises a plurality of aligned teeth having opposing wall angles of 90°.

6. A portable surgical workstation as claimed in claim 1 wherein said base defines a throughgoing slot with a stepped surrounding surface cut into a bottom surface of said base.

7. A portable surgical workstation as claimed in claim 1 wherein each of said jaw members has a miter section with an upper surface having with a top planar portion and a downward angled planar portion, said downwardly angled planar portion being provided with measuring indicia.

8. A portable surgical workstation as claimed in claim 1 wherein said drive means comprises a shaft with a smooth surface end portion defining a circular channel, a threaded central portion and an opposite smooth surface end portion, and a handle mounted on said opposite smooth surface end portion.

9. A portable surgical workstation as claimed in claim 8 wherein said handle defines an outwardly extending rib end.

10. A portable surgical workstation as claimed in claim 1 wherein said fixed jaw member defines a plurality of throughgoing bores running from a front face to a grasping face.

11. A portable surgical workstation for implant formation comprising a base, said base comprising a central planar section with integral handles extending away from said central planar section at an angle to the plane of said central planar section, a plurality of legs mounted to a bottom surface of said central planar section, said central planar section defining a plurality of tracks, a vise assembly mounted to said base, said vise assembly comprising a fixed jaw member secured to said base and a traveling jaw member moveably mounted to said base, said traveling jaw member defining a plurality of rail members adapted to be slidably mounted in said base tracks, a fixed drive housing mounted to said base, said fixed drive housing defining a threaded longitudinal bore which receives a threaded drive shaft, one end of said drive shaft being mounted in said traveling jaw member to preclude axial movement of said drive shaft within said traveling jaw member while retaining rotational movement, said drive shaft transporting said traveling jaw member toward and away from said fixed jaw member, each jaw member defining a slot which is axially aligned with the slot of the opposing member, each slot being of a width and depth to receive a surgical saw therein.

12. A portable surgical workstation as claimed in claim 11 wherein said drive shaft comprises a shaft with a smooth surface end portion defining a circular channel, a threaded central portion and an opposite smooth surface end portion, and a handle mounted on said opposite smooth surface end portion.

13. A portable surgical workstation as claimed in claim 11 wherein said base defines a throughgoing slot with a stepped recessed surrounding surface formed on a bottom surface of said base.

14. A portable surgical workstation as claimed in claim 11 wherein each of said jaw members has a section with an upper surface with a top planar portion and a downward angled planar portion, said downwardly angled portion being provided with measuring indicia.

15. A portable surgical workstation as claimed in claim 11 wherein said fixed jaw member and said traveling jaw member each define a grasping surface which is a knurled pattern, said knurled pattern surface comprises a plurality of aligned teeth having opposing wall angles of 90° and a pitch of about 0.2 mm.

16. A portable surgical workstation as claimed in claim 13 wherein a shoulder screw is mounted through said throughgoing slot into said traveling jaw member, said shoulder screw being provided with a head having a larger diameter than the width of said slot and being contained within said stepped surrounding surface.

17. A portable sterile standalone surgical workstation for implant formation comprising a base, said base comprising a central planar section with integral handles extending away from said central planar section at an angle to the plane of said central planar section, said handles defining at least one cutout section to aid grasping, said central planar section defining a plurality of tracks and a throughgoing slot with a recessed stepped surrounding surface formed on a bottom surface of said central planar section, a vise assembly mounted to said base, said vise assembly comprising a fixed jaw member secured to said base and a traveling jaw member moveably mounted to said base, said traveling jaw member defining a plurality of rail members adapted to be slidably mounted in said central planar section tracks, a fixed drive housing mounted to said base, said fixed drive housing defining a threaded longitudinal bore which receives a threaded drive shaft, one end of said drive shaft being secured in said traveling jaw member to preclude axial movement of said drive shaft within said traveling jaw member while retaining rotational movement, said drive shaft transporting said traveling jaw member toward and away from said fixed jaw member, each jaw member defining a slot traveling across the jaw member which is axially aligned with a slot of the opposing jaw member, said slots being of a width and depth to receive a surgical saw.

18. A portable sterile standalone surgical workstation as claimed in claim 17 wherein said traveling jaw member defines a plurality of throughgoing anchor pin bores running from a front face to a grasping face.

19. A portable sterile standalone surgical workstation as claimed in claim 17 wherein each of said jaw members has a section with an upper surface with a top planar portion and a downward angled planar portion, said downwardly angled portion being provided with measuring indicia.

\* \* \* \* \*